United States Patent [19]

Hamano et al.

[11] Patent Number: 5,112,807
[45] Date of Patent: May 12, 1992

[54] COMPOUND "LEUALACIN", ITS PREPARATION AND ITS USE IN THE TREATMENT OF CARDIOVASCULAR DISORDERS

[75] Inventors: Kiyoshi Hamano; Kouhei Furuya; Kazuhiko Tanzawa; Takeshi Kagasaki; Masaaki Miyamoto; Takeshi Kinoshita, all of Tokyo, Japan

[73] Assignee: Sankyo Company, Limited, Tokyo, Japan

[21] Appl. No.: 403,117

[22] Filed: Sep. 5, 1989

[30] Foreign Application Priority Data

Sep. 5, 1988 [JP] Japan .................. 63-221960

[51] Int. Cl.$^5$ .............. A61K 37/02; C07K 7/50; C07K 7/54; C07K 11/02
[52] U.S. Cl. ................ 514/11; 514/821; 514/929; 530/317; 530/323; 530/800; 435/71.1; 435/171; 435/911
[58] Field of Search ........... 530/317, 323, 800; 514/9, 929, 11, 821; 424/122; 435/171, 71.1, 911

[56] References Cited

U.S. PATENT DOCUMENTS 4,285,857  8/1981  Chipens et al. .................. 530/317

FOREIGN PATENT DOCUMENTS 2108106A  5/1983  United Kingdom.

OTHER PUBLICATIONS

Helms et al., J. Org. Chem. vol. 53, pp. 1298–1307 (1988).
Chemical Abstracts, Stasch et al., Dec. 7, 1987, vol. 107, No. 23 p. 28, col. 1, abstract-no. 211 620t & J. Hypertens, 1986 "Effect on hypertension cardiac hypertrophy and atrial natriuretic peptides of treatment with nitrendipine in SHR".
Chemical Abstracts, Helms et al, Apr. 11, 1988, vol. 108, No. 15, p. 414, col. 2, Abstract No. 128 158y & J. Org. Chem. 1988, 53(6) 1298-307 "Scytonemin A. and novel calcium antagonist from a blue-green alga".
Chemical Abstracts, Smolen et al, Dec. 3, 1984, vol. 101, No. 23, vol. 101, p. 410, col. 1, abstract-no. 208 214j & J. Lab. Clin. Med. 1984, "Lag period for superoxide anion generation and lysosomal enzyme release from human neutrophils: effects of calcium antagonists and anion channel blockers".

*Primary Examiner*—Christina Chan
*Attorney, Agent, or Firm*—Frishauf, Holtz, Goodman & Woodward

[57] ABSTRACT

A new compound, which we have named "Leualacin" has the formula (I):

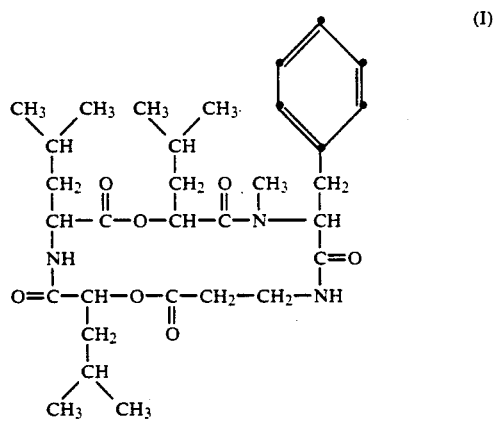

and may be prepared by cultivation of a microorganism of the genus Hapsidospora, especially *Hapsidospora irregularis*. The compound may be used for the treatment and prophylaxis of cardiovascular diseases and disorders, especially hypertension.

4 Claims, 4 Drawing Sheets

COMPOUND "LEUALACIN", ITS PREPARATION AND ITS USE IN THE TREATMENT OF CARDIOVASCULAR DISORDERS

BACKGROUND TO THE INVENTION

The present invention relates to a new compound which we have named "Leualacin" and which may be produced by fermentation using appropriate strains of microorganisms of the genus *Hapsidospora*, especially *Hapsidospora irregularis*. The invention also provides processes for the production of this new compound as well as compositions and methods using it for the treatment and prophylaxis of cardiovascular diseases and disorders. It also discloses a strain of microorganism of the species *Hapsidospora irregularis*, which may be used to produce the new compound.

It is now well established that the influx of calcium ions into certain cells in the mammalian body, including the smooth muscle cells of the vascular system and the myocardial cells, participates in the activity of such cells and that the dihydropyridine-sensitive calcium channel, which is situated on the cell surfaces of skeletal muscles and the myocardium, plays a role in regulating the influx of calcium ions into the cells. Hence, the administration of calcium channel blockers (also known as calcium antagonists), which inhibit such influx, would suppresses myocardial contractile force and rate and cause vasodilation. The calcium channel blockers are, therefore, useful in the treatment and prophylaxis of a variety of diseases and disorders of the heart and vascular system, such as angina pectoris, myocardial infarction, arrhythmia, hypertension, cerebrovascular spasm and other ischemic diseases and disorders.

It has been disclosed that verapamil (trade name "VASOLAN", a product of Eisai Co., Ltd.) and other calcium channel blockers inhibit the binding of $^3$H-nitrendipine to the calcium channels of the cell membrane. It is, therefore, thought that other substances that inhibit the binding of nitrendipine to the calcium channel of the cell membrane might also be useful as calcium channel blockers. As a result of its blocking the calcium channels, a calcium channel blocker suppresses any increase in intracellular calcium concentration and protects the patient against coronary spasm and dilation of the blood vessels.

A number of compounds having calcium channel blocking activity is known, for example certain dihydropyridine derivatives, such as nifedipine (trade name "ADALAT", a product of Bayer Yakuhin Co., Ltd.) and nicardipine, and other compounds, such as verapamil (mentioned above), diltiazem and flunarizine. Of these, nifedipine, nicardipine and diltiazem are widely used but are structurally unrelated to the compounds of the present invention. Verapamil and flunarizine are also structurally unrelated to the compounds of the present invention. Moreover, all of these known compounds are chemically synthesized compounds, whereas the compound of the present invention is a "natural" product, in that it is the product of fermentation. Only one prior "natural" product is known to us to have calcium antagonist activity, and that, like the compound of the present invention, is a cyclic peptide. This known compound is Scytonemin A, which was disclosed in the Journal of Organic Chemistry, 53, 1298-1307 (1988), but this compound has not yet been used clinically. Moreover, although it is a cyclic peptide, it has, as can be seen from the aforesaid article, a wholly different structure from that of the compound of the present invention and it is produced by a blue-green alga of the genus *Scytomenin*, whereas the compound of the present invention is produced by a mold of the genus *Hapsidospora*.

BRIEF SUMMARY OF THE INVENTION

It is, therefore, an object of the present invention to provide, as a new composition of matter, a cyclic peptide compound having calcium channel blocking activity and which we have named "Leualacin".

It is a further and additional object of the invention to provide a process for preparing the compound "Leualacin".

Other objects and advantages of the invention will become apparent as the description proceeds.

Leualacin has the formula (I):

The invention also provides a process for preparing Leualacin by culturing a Leualacin-producing strain of microorganism of the genus *Hapsidospora* and recovering Leualacin from the cultured broth.

The invention still further provides a method for the treatment or prophylaxis of cardiovascular diseases and disorders in an animal, especially a mammal, which may be human, suffering from or prone to such a disease or disorder by the administration thereto of an effective amount of a calcium channel blocker, wherein said calcium channel blocker is Leualacin.

DETAILED DESCRIPTION OF INVENTION

Leualacin has the molecular structure shown above and the following chemical and physical properties:

1) Description: neutral, fat-soluble.
2) Melting point: 140° C.
3) Specific optical rotation: $[\alpha]_D^{20}$ −102° (c 1.14, methanol).
4) Elemental analysis:
 Found: C, 64.65%; H. 8.33%; N, 7.21%.

Calculated: C. 64.90%; H, 8.26%; N, 7.32%.

5) Molecular weight: 573 (measured by mass spectrometry).

6) Molecular formula: $C_{31}H_{47}N_3O_7$ (measured by high resolution mass spectrometry).

Figure 1:
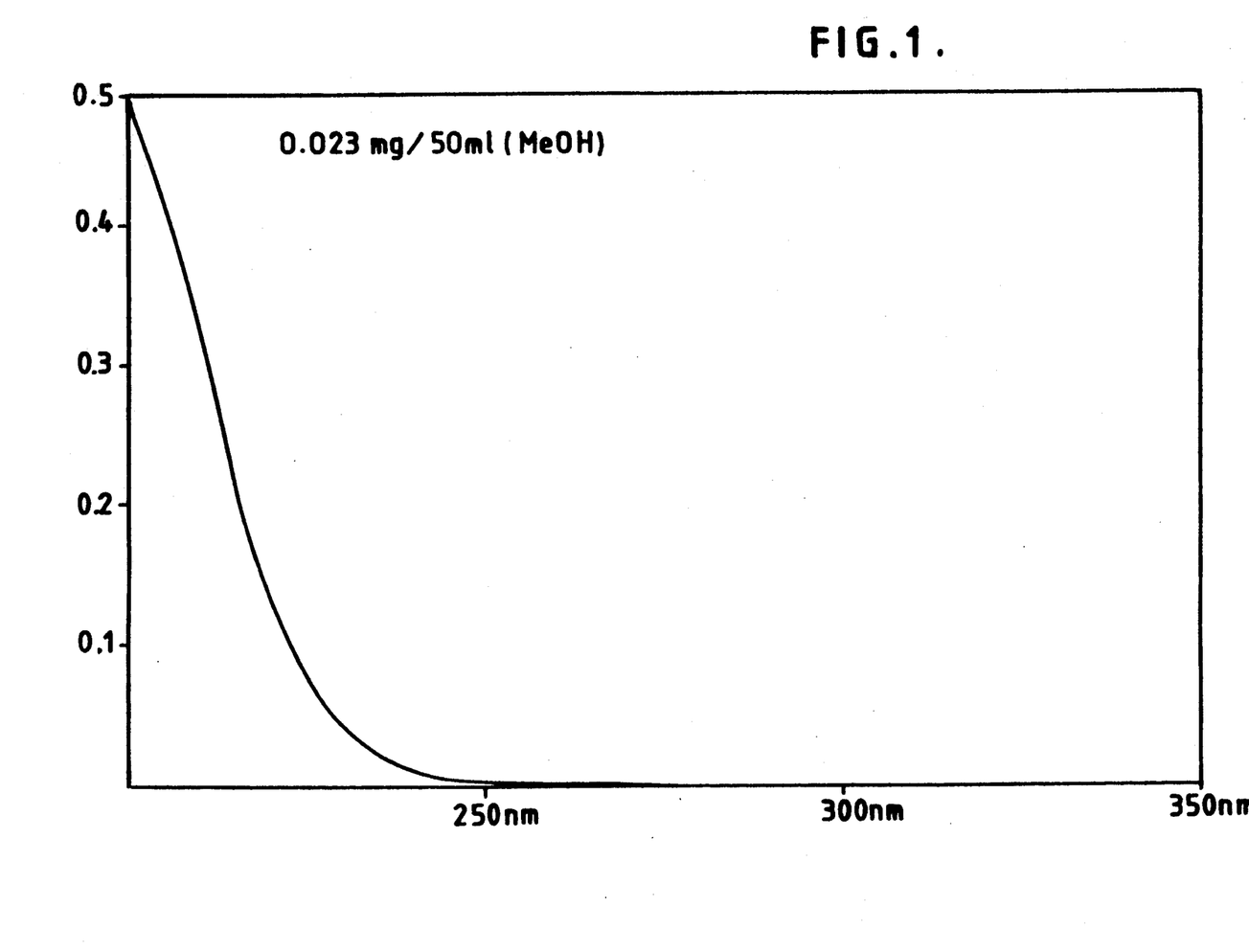
FIG. 1 shows the Ultraviolet Absorption Spectrum of Leualacin.

7) Ultraviolet absorption spectrum: The ultraviolet absorption spectrum measured in methanol is shown in FIG. 1 of the accompanying drawings.

Figure 2:
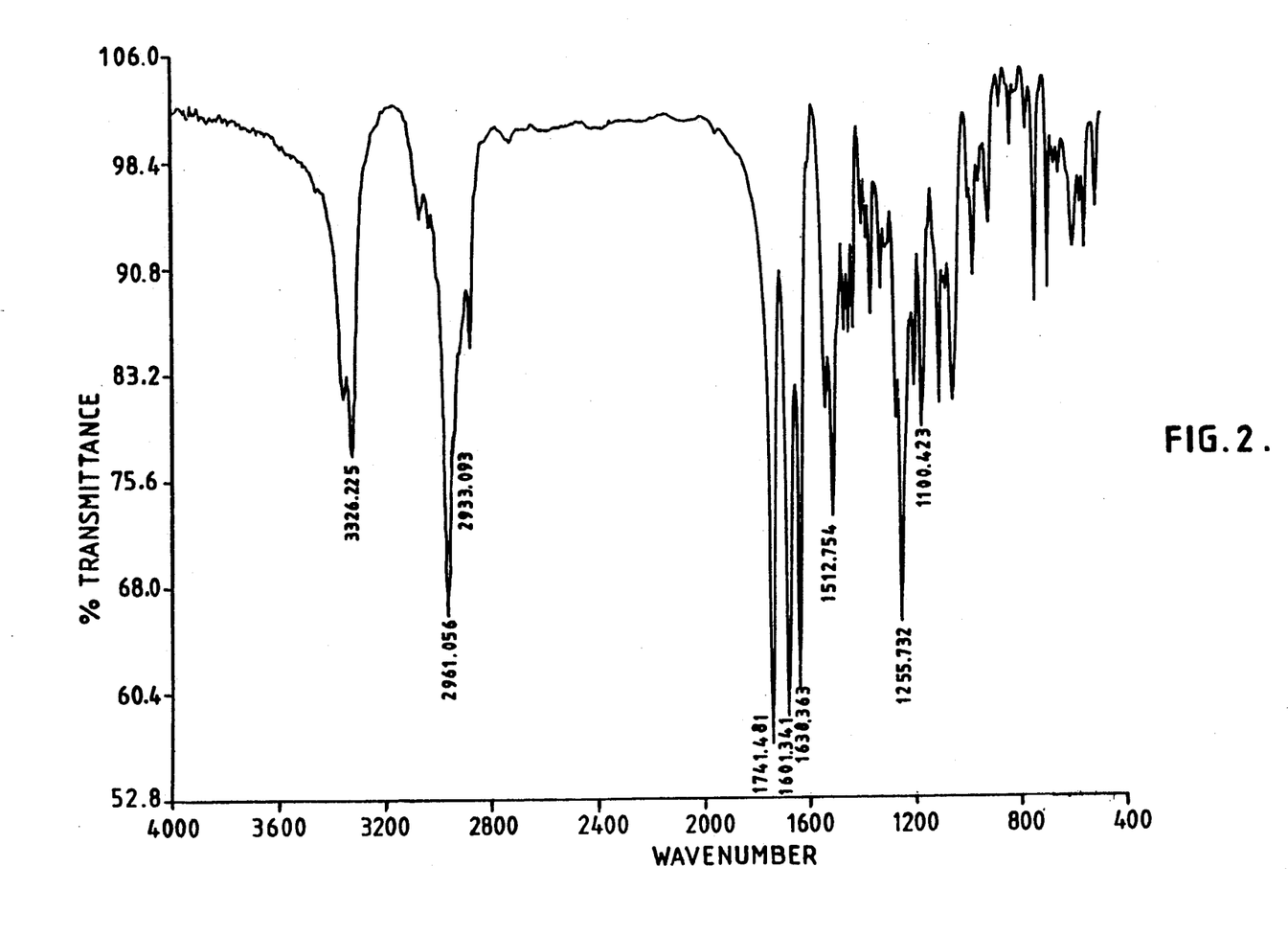
FIG. 2 shows the Infrared Absorption Spectrum of Leualacin.

8) Infrared absorption spectrum: The infrared absorption spectrum measured on a potassium bromide pellet is shown in FIG. 2 of the accompanying drawings.

Figure 3:
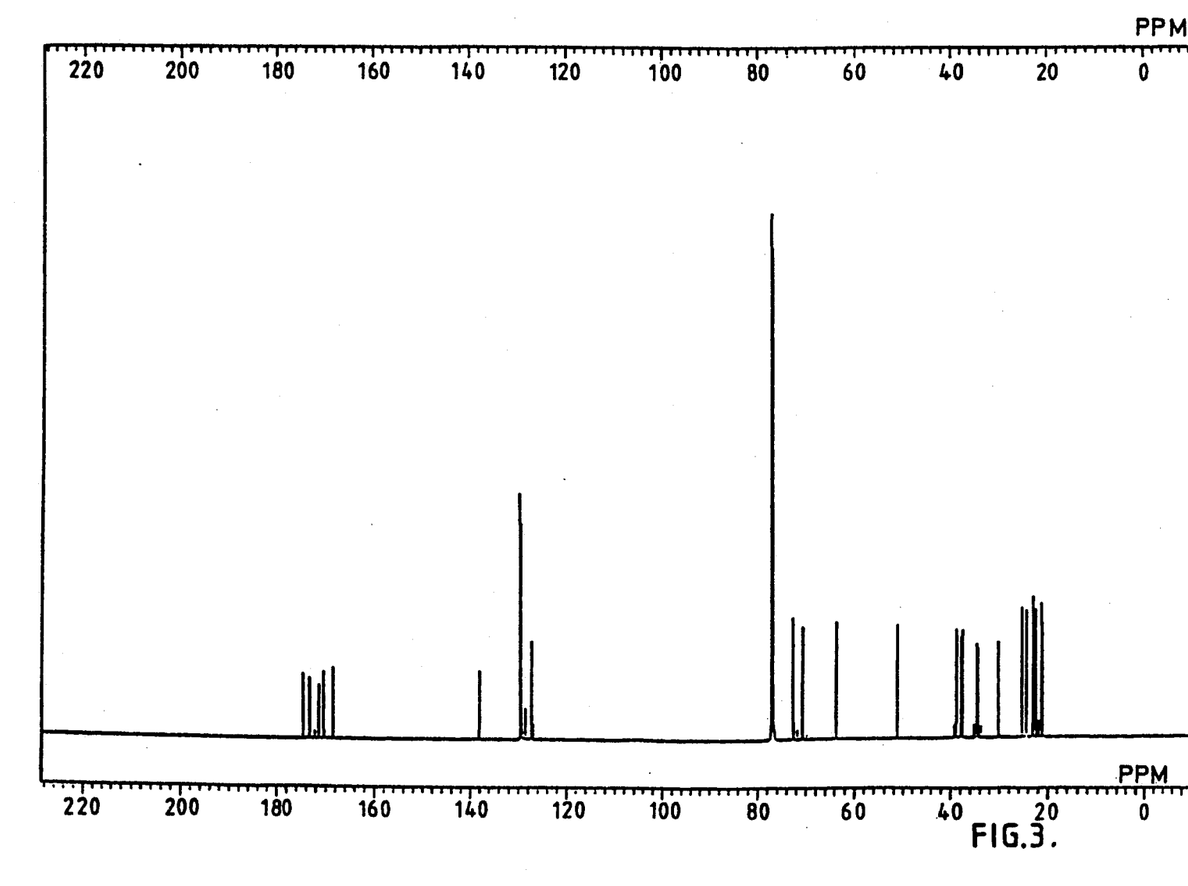
FIG. 3 shows the $^{13}$C Nuclear Magnetic Resonance Spectrum of Leualacin.

9) $^{13}$C-NMR spectrum: The nuclear magnetic resonance spectrum (at 125 MHz) measured in deuterochloroform using tetramethylsilane as an internal standard is shown in FIG. 3 of the accompanying drawings. Under the experimental conditions used, the signal of the solvent (CDCl$_3$) appeared to center at 77.1 ppm. Further, and consistent with the mass spectrometry data, the signals of 31 carbon atoms were observed.

Figure 4:
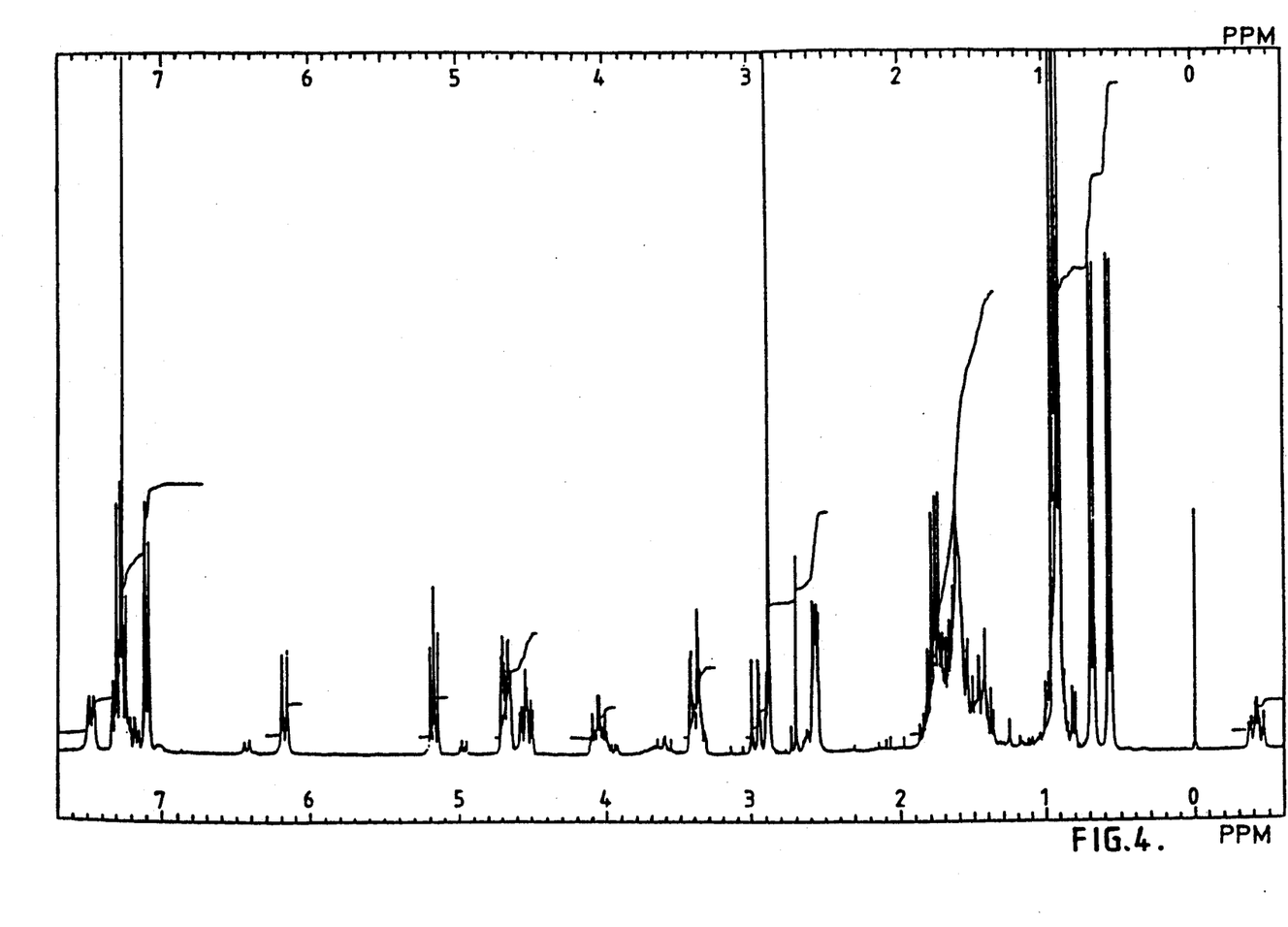
FIG. 4 shows the $^1$H Nuclear Magnetic Resonance Spectrum of Leualacin.

10) $^1$H-NMR spectrum: The nuclear magnetic resonance spectrum (at 270 MHz) measured in deuterochloroform using tetramethylsilane as an internal standard is shown in FIG. 4 of the accompanying drawings.

11) Solubility: Soluble in methanol, acetone, chloroform and ethyl acetate; insoluble in water.

12) High performance liquid chromatography: Column: RADIALPACK NOVAPACK cartridge C18, particle size 4 μm, column size 8 mm×10 cm (Waters Co., Ltd.);

Mobile phase: A 7:3 by volume mixture of acetonitrile and water;

Flow rate: 2 ml/min;

Detection: UV, 210 nm;

A peak is detected at 5.7 minutes at a column temperature of 25° C.

13) Acid hydrolysis: Acid hydrolysis of the compound gives leucine, N-methylphenylalanine, β-alanine and leucinic acid.

The systematic name of Leualacin in accordance with the recommendations of the International Union of pure and Applied Chemistry (IUPAC) is 11-benzyl-2,5,8-triisobutyl-10-methyl-1,7-dioxa-4,10,13-triazacyclohexadecane-3,6,9,12,16-pentone. However, also in accordance with the recommendations of the IUPAC, the compound is hereafter known by its trivial name "Leualacin".

In one embodiment of the present invention, the following isomer of Leualacin has been found to be produced, as shown in formula (II):

(II)

i.e. 11(S)-benzyl-2(R),5(S),8(S)-triisobutyl-10-methyl-1,7-dioxa-4,10,13-triazacyclohexadecane-3,6,9,12,16-pentone.

However, there are, as shown above, many asymmetric carbon atoms in the molecule of this compound, and, accordingly, many stereoisomers are possible. The present invention embraces all such isomers, whether isolated or as mixtures. Where the compound is produced as a mixture of isomers, it may be used as such a mixture or the individual isomers may be separated and used separately.

Leualacin has been produced by a strain of microorganism, which we have designated strain SANK 17182. This Leualacin-producing microorganism of the strain SANK 17182 employed in the present invention is a microorganism of the family Ascomycetes and was isolated by us from the soil at Manigaon in the Kingdom of Nepal. The microbiological properties of the Leualacin-producing strain, SANK 17182, are as follows:

Morphological characteristics

The growth on Weizmann agar medium is slow; the colony attains a diameter of 15 mm in 7 days and 35 mm in 14 days at 25° C. The surface of the colony is plane and white (White, 1-1-A) to light yellowish white (Yellowish white, 1-2-A). The reverse of the colony is also colorless to light yellowish white.

Ascocarps are dark brown in color; formed a little in the centre of the colony; superficial, globose to subglobose, nonostiolate; and 250–400 μm in diameter.

Asci: 8-spored; globose to subglobose, translucent, evanescent; and 8–15 μm in diameter.

Ascospores: globose with reticulated surfaces; dark brown in color; without germ pores; and 4–6 μm in diameter.

The anamorph is an *Acremonium* sp. and conidia are formed in wet masses at the tips of the phialides.

Conidia: hyaline, translucent; ellipsoidal to oval of dimensions from 3.5 to 10.0×2.0 to 3.5 μm.

By comparing the above morphologial characteristics with those of known species, a reasonable match was observed with those of *Hapsidospora irregularis*, which is described in the Canadian Journal of Botany, 48, 1815–1825 (1970). by D. Malloch and R. F. Cain. Accordingly, the strain employed in the present invention was identified as a known strain, *Hapsidospora irregularis* Malloch et Cain. and was assigned the company code number SANK 17182. The color expressions and codes used herein were assigned according to the directions in the Methuen Handbook of Color, 3rd Ed. (1978). written by A. Kornerup and J. H. Wanscher, and published by Eyre Methuen, London.

The strain was deposited by us at the Fermentation Research Institute, Tokyo, Japan with the accession No. FERM p-10199 and was redeposited under the conditions prescribed by the Budapest Treaty on 12 Jul. 1989 under the accession No. FERM BP-2511.

It has been established that strain SANK 17182 produces Leualacin. However, as is well known, the properties of fungi in general can vary considerably and such fungi can readily undergo mutation, both through natural causes and as the result of induction by artificial means. Accordingly, the process of the present invention embraces the use of any microorganism which can be classified within the genus *Hapsidospora*, especially *Hapsidospora irregularis*, and which shares with the strain SANK 17182 the characteristic ability to produce Leualacin. It is a matter of simple experimentation to determine, on the basis of the information given herein regarding the properties of Leualacin, whether any given strain produces Leualacin or produces it in sufficient quantity to render that strain of potential commercial interest.

The novel compound, Leualacin, of the present invention may be prepared by the culture of these strains of fungus in culture media of the type conventionally used for the production of other fermentation products from similar microorganisms. Such media necessarily contain microbiologically assimilable sources of carbon and of nitrogen as well as inorganic salts, as is well known to those skilled in the art.

Preferred examples of carbon sources include: glucose, fructose, maltose, sucrose, mannitol, glycerol, dextrin, oat, rye, corn starch, potato starch, corn meal, soybean meal, cottonseed cake, molasses, citric acid, tartaric acid and the like. Such compounds can be used alone or in any suitable combination. In general the amount used may vary in the range of from 1 to 10% by weight of the culture medium.

Preferred nitrogen sources are normally protein-containing materials such as are commonly used in a fermentation process. Examples of such nitrogen sources include: soybean meal, wheat bran, peanut meal, cottonseed cake, cottonseed meal, casein hydrolyzates, pharmamin, fish meal, corn steep liquor, peptone, meat extract, yeast, yeast extract, malt extract, sodium nitrate, ammonium nitrate, ammonium sulfate and the like. These nitrogen sources may be used alone or in any suitable combination. In general, we prefer to employ them at a concentration between 0.2 and 6% by weight of the culture medium.

The nutritive inorganic salts that should be added to the culture medium are conventional salts that are capable of providing various ions necessary to the growth of microorganisms, such as sodium, ammonium, calcium, phosphate, sulfate, chloride and carbonate ions. In addition, the medium should contain minor amounts of essential metals, such as potassium, calcium, cobalt, manganese, iron and magnesium.

When the process of the present invention is carried out by a liquid culture technique, an antifoaming agent, such as a silicone oil, plant oil or surface-active agent, is preferably used in the culture medium. The pH of the culture medium for producing Leualacin by the cultivation of *Hapsidospora irregularis* Malloch et Cain, SANK 17182. preferably varies within the range of from 5.0 to 8.0.

The cultivation may be carried out at any temperature within the range of from 15 to 35° C., although a temperature of from 22 to 35° C. is preferred for good growth, and a temperature of from 22 to 28° C. is preferred in order to optimise the production of Leualacin.

Leualacin is produced under aerobic culture conditions and conventional aerobic culture methods, such as solid culture, shaking culture and aeration-stirring (submerged) culture methods, may be used. In the case of small scale cultivation, shaking culture for a few days at 26° C. is typical. In such a small scale culture method, the culture may be initiated with 1 or 2 proliferation steps, producing seed cultures in, for example, Erlenmeyer flasks, fitted with baffle plates, which serve as a liquid flow regulator. The medium for the seed culture steps preferably contains both carbon and nitrogen sources. In the preferred sequence of operations for such small scale cultivation, the seed culture flasks are shaken in a constant temperature incubator at 26° C. for 7 days or until sufficient growth is achieved. The grown seed culture is then transferred to a second seed medium or to the production medium. When an intermediate growth phase is used, essentially the same method is used for growth and an aliquot of the resulting intermediate product is inoculated into the production medium. The inoculated flask may be incubated for several days whilst shaking, and, after completion of the incubation, the contents of the flask may be centrifuged or filtered.

In the case of large scale production, the use of an appropriate fermentor equipped with a stirrer and an aeration apparatus is preferred. In this case, the nutritive medium can be prepared inside the fermentor. The medium is preferably sterilized by elevating the temperature to 125° C.; after cooling, the sterilized medium may be inoculated with the previously prepared seed culture. The culture then proceeds under stirring and aeration at 26° C. This method is suitable for obtaining the compound of the present invention in a large amount.

The progress of the cultivation and the amount of Leualacin produced as the culture proceeds can be determined by a radio ligand binding assay method, that is, for example, the method of G. A. Weiland and R. E. Oswald [Journal of Biological Chemistry, 260, 8456–8464 (1985)] which is based on the ability of Leualacin to inhibit the binding of $^3$H-nitrendipine to microsomes. High performance liquid chromatography may also be used. Generally, the amount of Leualacin reaches a maximum between 72 and 150 hours after initiation of the fermentation, but the exact time will vary depending upon the temperature and other fermentation conditions; however, the exact optimum time for any set of conditions can easily be determined by following the production of Leualacin, as suggested above.

The Leualacin may be recovered from the cultured broth by conventional means well known for recovering from fermentation broths compounds of this type, which are both retained in the microbial cells and released into the culture medium. For example, after completion of the culture, the mycelium and other solid materials containing Leualacin may be separated from the broth by filtration, generally with a filter aid, for example diatomaceous earth, or by centrifugation, and the Leualacin present in the filtrate or the supernatant, as well as that in the mycelium, can be recovered by extraction and purification processes utilizing the physicochemical properties of Leualacin. For example, the Leualacin present in the filtrate or the supernatant can be extracted and purified under neutral pH conditions by partitioning the Leualacin between water and a single immiscible organic solvent or a mixture of such solvents, for example ethyl acetate, hexane, chloroform, ethylene chloride or methylene chloride. Another method is to use an adsorption agent, for example activated charcoal, or an adsorption resin, such as AMBERLITE (trade mark) XAD-2 or XAD-4 (Rohm and Haas Co., Ltd.), or DIAION (trade mark) HP-10, HP-20, CHP-20P or HP-50 (Mitsubishi Kasei Corporation). The fluid containing the Leualacin is passed through a layer of one of these adsorbents in order to remove the adsorbed impurities or the adsorbed Leualacin is eluted with a suitable eluent, such as aqueous methanol, aqueous acetone or aqueous butanol. The Leualacin present in the mycelium may be extracted with aqueous acetone or methanol containing from 50 to 90% by volume water, after which the organic solvent is removed and methods of extraction and purification similar to those for the filtrate can be applied.

Leualacin obtained as described above can be further purified by various conventional techniques, notably the various chromatography techniques, such as adsorption column chromatography using a carrier such as silica gel or a magnesia-silica gel, such as FLORISIL (trade mark), partition column chromatography using SEPHADEX (trade mark) LH-20 (Pharmacia Fine Chemicals), or high performance liquid chromatography using a column for a normal or reverse phase process.

Leualacin, the compound of the present invention, is a novel compound which has not previously been reported and which shows calcium antagonistic action in test animals and which is expected to do so also in other animals (e.g. humans, dogs, cats, rabbits, etc.). It is therefore expected to be useful for the prophylaxis or therapy of hypertension, arrhythmia, heart failure and angina pectoris in all animals, especially mammals, and notably humans.

Leualacin may be used alone as a pharmaceutical drug, or it may be mixed with pharmaceutically acceptable carriers and/or excipients and/or diluents appropriate to its intended route of administration, as is well known in the art. For example, for oral administration, it may be employed in the form of powders, granules, tablets or capsules; for parenteral administration, it may be employed in the form of injections. The dosage of the compounds will vary, depending upon the severity and nature of the disease of disorder, the age, body weight and condition of the patient and upon the route, frequency and period of administration. However, a suitable daily dose of Leualacin for an adult human would be in the range of from 0.01 to 2.0 g. which may be administered as a single dose or as divided doses e.g. from one to three times per day.

The preparation of the compound of the present invention is further illustrated by the following non-limiting Examples.

EXAMPLE 1

A) Culture

One loopful of a culture of *Hapsidospora irregularis* Malloch et Cain, SANK 17182, was aseptically inoculated into a 500 ml Erlenmeyer flask, fitted with baffles, (seed flask) containing 100 ml of a sterilized medium having the composition described below. The inoculated flask was then incubated on a rotary shaking apparatus at 200 rpm (radius of gyration: 7 cm) at 26° C. for 7 days.

| Composition of Medium | |
|---|---|
| Sucrose | 20 g |
| Potato (raw and mashed) | 100 g |
| Casamino acid (vitamin-free) | 10 g |
| Potassium phosphate, monobasic | 5 g |
| Magnesium sulfate (7H$_2$O) | 2.5 g |
| Deionized water | 1000 ml | pH: not adjusted 100 ml of a medium having the same composition as that shown above was placed into each of twenty 500 ml Erlenmeyer flasks. After sterilisation of the flasks and contents, 2 ml of the grown mycelia of the seed culture were inoculated into each of the flasks. The 20 flasks were then incubated on a rotary shaker for 7 days under the same conditions as were used for the seed culture.

B) Isolation

The whole mass of the cultured broth was centrifuged at 3,000 rpm for 20 minutes. The precipitate was reserved for later extraction. The pH of the supernatant (1.7 liters) was adjusted to a value of 7.0, and the liquid was transferred into a separating funnel and extracted twice, each time with 2 liters of ethyl acetate. The ethyl acetate extracts were combined and washed with 3 liters of a saturated aqueous solution of sodium chloride, after which they were dried over anhydrous sodium sulfate, and concentrated to dryness under reduced pressure using a rotatory evaporator, to give 273 mg of an oil.

Meanwhile, the aforementioned precipitate containing the mycelia was mixed with 300 ml of acetone and stirred for 1 hour. At the end of this time, the resultant mixture was filtered and the acetone was distilled under reduced pressure from the filtrate, using a rotatory evaporator. The residue was mixed with water to make up the volume to 1000 ml, and the resulting mixture was adjusted to a pH value of 7.0 by the addition of sodium hydroxide. The mixture was then extracted twice, each time with 1000 ml of ethyl acetate. The ethyl acetate extracts were combined and washed with 2 liters of a saturated aqueous solution of sodium chloride, after which they were dried over anhydrous sodium sulfate, and concentrated to dryness under reduced pressure in a rotatory evaporator, to afford 391 mg of an oil.

The oily substance (273 mg) obtained from the culture filtrate and the 391 mg of oil obtained from the mycelium were combined, to give a total of 664 mg of oil. The whole of this was dissolved in a 4:6 by volume mixture of hexane and ethyl acetate. The oil in the solution was purified by column chromatography, using a column packed with silica gel (LOBAR Column, Art. 10401 LICHROPREP Si60, size B, Merck AG.) which had been pre-equilibrated with a 4:6 by volume mixture of hexane and ethyl acetate. At a flow rate of 10 ml/minute, using a differential refractometric detector, all fractions corresponding to the peaks detected were separately collected. Each of the fractions was evaporated to dryness under reduced pressure in a rotatory evaporator. Each of the resultant fractions was assayed to determine its activity by means of the radioligand binding assay method described hereafter in Experiment 1. An effective calcium blocking activity was found in 100 mg of fractions with retention times of from 30 to 37 minutes, and the IC$_{50}$ value was as high as 1.38 µg/ml. When an aliquot of this active fraction was applied to a high performance liquid chromatography [column: RADIALPACK NOVAPACK cartridge C18, particle size 4 µm, column size 8 mm×10 cm (Waters Ltd.); mobile phase: a 7:3 by volume mixture of acetonitrile and water; flow rate 2 ml/minute; detection wave length: UV 210 nm; column temperature: 25° C.], a single peak with a terminal UV absorption was observed at 5.7 minutes.

The resulting active fraction was then purified by reverse phase liquid chromatography. Specifically, the whole mass, dissolved in 200 µl of acetonitrile, was applied to a SENSHU PACK ODS H-5251 (20 mm i.d.×250 mm. Senshu Kagaku Co., Ltd.) column. The development and elution were carried out with 60% v/v aqueous acetonitrile, and those fractions which a differential refractometric detector showed as a peak eluated at 28 minutes were collected. The fractions were then concentrated to dryness under reduced pressure in a rotatory evaporator to give a 70 mg of pure Leualacin as a white powder. The powder was then crystallized from a mixture of acetone and hexane to afford 40 mg of colorless needles.

The product obtained had the properties listed above and has been found to be the isomer having the formula (II), shown above.

EXAMPLE 2

A) Culture

A large scale fermentation of *Hapsidospora irregularis* Malloch et Cain, SANK 17182, was conducted to obtain Leualacin. The seed medium used had the following composition:

| Composition of seed medium | |
| --- | --- |
| Sucrose | 20 g |
| Potato | 100 g |
| Casamino acid (vitamin-free) | 10 g |
| Potassium phosphate, monobasic | 5 g |
| Magnesium sulfate (7H$_2$O) | 2.5 g |
| Antifoaming agent (CB-442) | 0.2 g |
| Deionized water | 1000 ml | pH: not adjusted 100 ml of this medium was added to a 500 ml Erlenmeyer flask, fitted with baffles, and the medium was sterilized at 120° C. for 20 minutes. At the end of this time, spores of *Hapsidospora irregularis* Malloch et Cain, SANK 17182, were added by aseptic inoculation to the flask, and the microorganism was cultured at 200 rpm on a rotatory shaker at 26° C. for 7 days.

15 liters of the same medium as was used for the seed culture were poured into each of two 30 liter jar fermentors, which were then sterilized at 120° C. for 30 minutes. Two hundred ml of the above-mentioned seed culture was then inoculated into each of the jar fermentors and an aeration-agitation culture was continued at 26° C. for 6 days, while controlling the agitation rate automatically within the range between 100 and 300 rpm and at an air flow rate of 7.5 l/minute, in order to maintain the dissolved oxygen concentration at from 0.3 to 0.5 ppm.

B) Isolation

About 3 kg of a CELITE (trade mark) filter aid were added to 15 liters of the whole mass of the cultured broth of SANK 17182 obtained as described above, and the mixture was filtered through a filter press to obtain a filtrate and a mycelial fraction. 35 liters of acetone were then added to 8 kg of the mycelial cake, and then the mixture was stirred at room temperature for 1 hour. At the end of this time, the mixture was filtered to separate the filtrate and the mycelium. Again, 15 liters of 80% v/v aqueous acetone were added to the mycelial fraction, and the mixture was extracted, whilst stirring for 1 hour. The mixture was then filtered, and the resulting filtrate was combined with the filtrate obtained previously. The combined filtrates were evaporated in a rotatory evaporator under vacuum to expel the acetone and to yield 10 liters of an aqueous solution. The pH of the aqueous solution was adjusted to a value of 6.5 by the addition of a 4N aqueous solution of sodium hydroxide, and then the solution was extracted twice, each time with 10 liters of ethyl acetate; 18 liters of an ethyl acetate solution was obtained. This solution was washed with 15 liters of a saturated aqueous solution of sodium chloride, and then dehydrated with 800 g of anhydrous sodium sulfate. It was then concentrated to dryness in a rotatory evaporator under vacuum, to give 21.2 g of an oily material. This oily material was dissolved in 80 ml of a 4:6 by volume mixture of hexane and ethyl acetate, and the solution (divided into 4 approximately equal parts) was applied to a silica gel column (LOBAR column, Art. 10402 LICHROPREP Si60, size C, Merck AG), which had previously been equilibrated with a 4:6 by volume mixture of hexane and ethyl acetate. At each of the applications, the same solvent was used for the elution and the fractions which showed peaks, indicated by a differential refractometer connected to the column, at 35–50 minutes were collected. In the same manner as described in Example 1, the purities of these fractions were monitored by means of HPLC and the activities were confirmed by a radioligand binding assay method. The fractions were then evaporated to dryness under vacuum in a rotatory evaporator, to give a total of 1.8 g of oily material. This oily material was then purified by reverse phase liquid chromatography. Specifically, the oily material, dissolved in 8 ml of acetonitrile and divided into 10 aliquots, was applied to a reverse phase column of SENSHU PACK ODS H-5251 (20 mm i.d. ×250 mm, Senshu Kagaku Co., Ltd.). The column was eluted with a 60:40 by volume mixture of acetonitrile and water at a flow rate of 7.0 ml/minute, and the eluates were monitored with a differential refractometer. That fraction showing a peak at 28 minutes was collected and evaporated to dryness in a rotatory evaporator under reduced pressure, to give 1.66 g of pure Leualacin as a colorless oily material. This oily material was further triturated with a mixture of acetone and hexane to cause crystallization of 800 mg of Leualacin as colorless needles.

EXPERIMENT 1

Radioligand Binding Assay Method

This experiment used a radioligand binding assay method, which is a modification of the method of G. A. Weiland and R. E. Oswald [Journal of Biological Chemistry, 260, 8456–8464 [(1985)], to determine the activity which inhibits the binding of $^3$H-nitrendipine to microsomes.

The reaction was carried out at 25° C. for 30 minutes in 1 ml of a reaction mixture comprising 15 to 20 μg of a microsome fraction prepared from porcine heart, 200 PM $^3$H-nitrendipine (NEN-Dupont Pharmaceuticals, specific activity 88.1 Ci/mM), 50 mM NaOH-HEPES buffer (pH 7.4) and 0.5% by volume ethanol. (HEPES is N-2-hydroxyethylpiperazine-N'-2-ethanesulfonic acid). Leualacin was dissolved at various concentrations in the ethanol and the serially diluted solution was added in a sufficient amount to make the ethanol concentration 0.5% in the reaction mixture. The result achieved with a reaction mixture using 1 μM of cold nitrendipine was employed as the control. After completion of the reaction, the reaction mixture was filtered on a glass-fibre filter (GF/C) and the fraction retained on the filter was washed with the aid of a Cell Harvester (Type M-24, Brandel Co., Ltd.). The glass-fibre filter was then put in a vial and OPTIFLUOR (Packard Co., Ltd.) was used as the scintillator and the radioactivity (as disintegrations per minute) was measured. Leualacin was found to have a potent ID$_{50}$ value which was as low as 0.99 μg/ml.

EXPERIMENT 2

Calcium Antagonizing Action in the Tenia Caecum

The calcium antagonizing activity in the tenia caecum was measured according to the method of M. Spedding [Naunyn-Schmiedeberg's Arch. Pharmacol. 318, 234-240(1982)]. Male guinea pigs weighing 250 to 300 g were laparotomized under pentobarbital anesthesia and the tenia was immediately removed from the caecum. The tenia was cut into strips of 6-7 cm length and suspended in a Magnus vessel filled with 20 ml of Tyrode's solution without calcium aerated with a mixed gas ($O_2$ 95%-$CO_2$ 5% by volume). After the specimen had eguilibrated by standing for 1 hour under the above conditions, 0.2 ml each of 30, 100 and 300 mM aqueous calcium chloride solutions were cumulatively added at 3 minute intervals and the contraction of the specimen was measured. After the measurements, the specimen was washed twice with Tyrode's solution without calcium and left for 30 minutes. The specimen was then incubated with Leualacin for 30 minutes, after which 0.2 ml each of 30, 100 and 300 mM calcium chloride solutions were cumulatively added at 3 minute intervals in the same manner as above, and the contraction was again measured. The contraction after the treatment with the Leualacin solution was deducted from that after the treatment with the calcium chloride solution alone and the value obtained was divided by the contraction after the treatment with the calcium chloride solution alone, to give the antagonizing rate.

The results were as shown in Table 1:

TABLE 1

| Concentration of Leualacin (g/ml) | Antagonizing rate (%) |
|---|---|
| $10^{-9}$ | 0 |
| $10^{-8}$ | 22 |
| $10^{-7}$ | 73 |
| $10^{-6}$ | 97 |

As is clear from the above results, Leualacin showed a potent antagonistic activity.

EXPERIMENT 3

Antihypertensive activity

Male SHR (spontaneously hypertensive rats), 15 weeks old, were anesthetized with sodium pentobarbital (50 mg/kg intraperitoneally), and a polyethylene cannula was inserted through the left femoral artery into the abdominal aorta. The other end of the cannula was led out of the body and fixed at the back of the neck. One week after the operation, when the animal had recovered from the stress of the surgery, the other end of the cannula was connected to a blood pressure transducer, which was constructed according to the directions of Laffan et al. [Laffan, P. J., Peterson A., Hitch S. W. and Jeunelot C., Cardiovascular Res. 6, 319-324 (1972)], but with slight modifications. The blood pressure and heart rate of the conscious and unstressed SHR were measured. After the blood pressure and the heart rate had stabilised for more than one hour, the test drug was administered by gavage. The test drug was dissolved in ethanol and diluted with physiological saline and administered at the dose shown in Table 2. After administration of the test sample, the blood pressure and the heart rate were measured every 15 minutes over a pressure thus determined is shown in Table 2.

TABLE 2

| Dose | Decrease of blood pressure (mmHg) |
|---|---|
| 100 μg/kg | 44 |
| 300 μg/kg | 57 |

As shown above, Leualacin showed an excellent antihypertensive activity.

EXPERIMENT 4

Acute Toxicity

No toxicity was noted when Leualacin was orally administered to mice at a dose of 200 mg/kg, which is far in excess of any reasonable therapeutic dose.

The following is an example of a pharmaceutical formulation.

| Capsules for oral administration | |
|---|---|
| Leualacin | 30 mg |
| Lactose | 170 mg |
| Corn starch | 148.8 mg |
| Magnesium stearate | 1.2 mg |
| | 350 mg |

The powders of the above formulation were mixed, and after being passed through 30 mesh (Tyler standard mesh) 350 mg of the powder was put in a gelatin capsule to prepare capsules.

We claim:

1. A compound of formula (I):

2. A compound of claim 1 having the formula (II):

(II)

3. A method for the treatment of hypertension in an animal comprising the administration thereto of an effective amount of a calcium channel blocker, wherein said calcium channel blocker is the compound as claimed in claim 1.

4. A method for the treatment of hypertension in an animal comprising the administration thereto of an effective amount of a calcium channel blocker, wherein said calcium channel blocker is the compound as claimed in claim 2.

* * * * *